United States Patent [19]

Lewis, Jr. et al.

[11] Patent Number: 4,533,496

[45] Date of Patent: Aug. 6, 1985

[54] METHOD OF ISOLATING MONOCLONAL ANTIBODIES FROM HYBRIDOMA CULTURES

[75] Inventors: Charles Lewis, Jr., Hazelwood; Jitka V. Olander, University City; William R. Tolbert, Manchester, all of Mo.

[73] Assignee: Monsanto Company, St. Louis, Mo.

[21] Appl. No.: 608,283

[22] Filed: May 8, 1984

[51] Int. Cl.$^3$ .................. C07G 7/00; C07G 7/028
[52] U.S. Cl. .................. 260/112 R; 435/68; 435/240; 435/241
[58] Field of Search ............ 260/112 R; 435/68, 240, 435/241, 948

[56] References Cited

U.S. PATENT DOCUMENTS 3,555,001 1/1971 Wallis et al. .................. 260/112 B
4,097,473 6/1978 Lewis et al. .................. 260/112 B
4,382,028 5/1983 Paget .................. 435/68

OTHER PUBLICATIONS

Reisfeld et al., Production and Characterization . . . Antigens, *Hybridoma in Cancer Diagnosis and Treatment,* (21), 1982 Raven Press, N.Y., (Ed., Mitchell et al.), p. 183.
Monoclonals Disappoint . . . Clinical Trials, *Newsweek,* May 1984, p. 8.
Bumal et al., Unique Glycoprotein . . . Human Melanoma Cells, *PNAS,* (vol. 79), 1982, pp. 1245–1249.
Bumal et al., Monoclonal Antibody . . . *in vivo* Tumor Growth, *PNAS,* (vol. 80), 1983, pp. 529–533.
Monoclonal Antibodies, Milstein, pp. 66–74.

*Primary Examiner*—John Kight
*Assistant Examiner*—Garnette D. Draper
*Attorney, Agent, or Firm*—Scott J. Meyer; James W. Williams, Jr.

[57] ABSTRACT

Monoclonal antibodies are isolated from spent culture medium of the *in vitro* growth of hybridoma cells by treating said spent cell culture medium or a concentrate thereof with a water-insoluble, cross-linked polyelectrolyte copolymer.

15 Claims, No Drawings

METHOD OF ISOLATING MONOCLONAL ANTIBODIES FROM HYBRIDOMA CULTURES

BACKGROUND OF THE INVENTION

This invention relates to the isolation of monoclonal antibodies.

The immune system provides an important mechanism for the resistance to infectious agents. The antibodies that are produced in response to the foreign substance (antigen) by the immune system also provide a good source of reagents for treatment of disease and for diagnostic purposes. Antibodies thus produced by the immune system have the characteristic of being heterogeneous.

With the advent of hybridoma technology first developed by Köhler and Milstein, it is now possible to generate monoclonal antibodies which are essentially homogeneous compositions having uniform affinity for a binding site. The production of mouse hybridomas by these investigators is described in Nature 256, 495–497 (1975); and Eur. J. Immunol. 6, 511–519 (1976). According to this method, tissue-culture adapted mouse myeloma cells are fused to spleen cells from immunized mice to obtain the hybrid cells that produce large amounts of a single antibody molecule. The fusion generally is carried out in the presence of polyethylene glycol (PEG) as described by Galfe et al., Nature 266, 550–52 (1977), followed by selection in HAT medium (hypoxanthine, aminopterin and thymidine) as described by Littlefield, Science 145, 709–10 (1964). Immunization can be carried out with virtually any foreign antigen of interest. These can be, for example, hormones, proteins, cell-surface antigens, tumor markers, viruses, bacteria, parasites and the like. The use of hybridomas to provide a wide variety of clinically important antigens is illustrated by the extensive list and references cited, for example, by Sevier et al., Clin. Chem. 27 (11), 1797–1806 (1981).

Monoclonal antibodies also can be generated from human cells. See, for example, Rosen et al., Cell 11, 139–47 (1977); Olsson and Kaplan, Proc. Nat. Acad. Sci. USA 77, 5429–31 (1980); Croce et al., Nature (London) 288, 488–91 (1980); Eur. Pat. Appl. No. 44,722, Jan. 27, 1982; and Eur. Pat. Appl. No. 62,409, Oct. 13, 1982. Such antibodies should have better tolerance in human immunotherapy than the antibodies raised in mice.

Once the desired hybridoma is successfully cloned it may be desired to culture the cells on a large scale for the production of monoclonal antibodies in bulk quantities. Useful methods for such large scale cultivation of mammalian cells for producing monoclonal antibodies are described by Feder and Tolbert, Sci. Amer. 248 (1), 24–31 (1983).

Typically, the hybridoma cells are grown in conventional cell culture media such as, for example, RPMI-1640 or Dulbecco's modified Eagle's medium. The medium is usually supplemented with serum. It is customary to include up to 15% fetal calf serum, but bovine and horse serum also can be used.

Another method of monoclonal antibody production is described in U.S. Pat. No. 4,409,331, which involves growing the hybridoma cells encapsulated in semipermeable membranes. HAT selection can be avoided according to this method since the fusion process is viewed under a microscope and the unsuccessful fusions can be discarded based on this visual observation.

Yet another means of producing monoclonal antibodies involves culture of the hybridomas on hollow fiber membranes as disclosed by Calabresi et al., Proc. AACR and ASCO, p. 302 (1981).

A somewhat different approach to the preparation of hybridomas which can be used for the production of monoclonal antibodies is by the electrofusion or cell fusion system of Zimmermann and Vienken, J. of Membrane Biol. 67, 165–82 (1982), Springer-Verlag, New York; Zimmermann, Biochim. Biophys. Acta 694, 227–77 (1982); and Bischoff et al., FEBS Letters, 147 (1), 64–8 (1982), Elsevier Biomedical Publishing Co. According to this method, the cells to be hybridized are exposed to a low-level, non-homogeneous, high frequency electric field which orients the cells into "pearl necklace" chains. A direct current pulse is then applied which opens micropores in adjoining cell membranes. This allows intermixing of the cellular contents and results in cell fusion. The electrofusion method thus eliminates the chemical trauma of polyethylene glycol and the biological harm of viral fusion in creating hybridomas for monoclonal antibody production.

After production of the monoclonal antibodies by cell culture, it is usually desired to isolate or purify the antibodies from the medium. Various known methods of such isolation include, for example, ammonium sulfate precipitation, dialysis, affinity chromatography on protein A-Sepharose ®, ion exchange on DEAE columns such as, for example, DEAE-Sephacel ®, DEAE-Biogel ® and DEAE Affi-Gel ® Blue, or affinity chromatography on anti-Ig-agarose. These and other such conventional methods of purification of monoclonal antibodies are described by Goding, J. Immunol. Meth. 39, 285–308 (1980); and Bruck et al., J. Immunol. Meth. 53, 313–19 (1982).

DESCRIPTION OF THE INVENTION

In accordance with the present invention, a novel method is provided for isolating monoclonal antibodies from cell culture media. The method comprises contacting spent cell culture medium, or a concentrate thereof, after culture of hybridoma cells for production of monoclonal antibodies, with water-insoluble, cross-linked polyelectrolyte copolymers. The contacting is carried out at pH levels and ionic salt concentrations such as to provide suitable sequential adsorption and desorption of protein on the polyelectrolyte copolymer. When the adsorbed monoclonal antibody is desired to be retained in a form bound to the polyelectrolyte copolymer, desorption may not be necessary. When unbound monoclonal antibody is desired and/or when further purification is desired, desorption preferably is carried out.

These polyelectrolyte copolymers are copolymers of olefinically unsaturated monomers having from 2 to about 4 carbon atoms and $\alpha,\beta$-unsaturated polycarboxylic acids or anhydrides having from 4 to about 6 carbon atoms and containing pendant diloweralkylaminoloweralkylimide functional groups.

As used herein, loweralkyl is defined to mean alkyl having from about one to about four carbon atoms.

Illustrative examples of suitable olefinically unsaturated monomers are ethylene, propylene and isobutylene; illustrative examples of suitable $\alpha,\beta$-unsaturated polycarboxylic acids or anhydrides are maleic, citraconic, itaconic and aconitic acids or anhydrides. Of these monomeric components, ethylene and maleic anhydride are preferred for the copolymeric formation.

The copolymer also will preferably contain substantially equimolar quantities of the two component monomers.

Cross-linking of the copolymers to provide water-insolubility can be carried out with conventional cross-linking agents such as, for example, divinylbenzene and ethylene diamine. The preferred cross-linking agents are loweralkyliminobis(loweralkylamines) in which loweralkyl is defined as above.

The polyelectrolyte copolymers used in the present invention are known compounds which can be made according to methods described in U.S. Pat. Nos. 3,554,985; 3,555,001; 4,081,432; 4,097,473; 4,118,554; and 4,157,431. For example, the preferred copolymers of ethylene and maleic anhydride (EMA) can be prepared by reacting ethylene and maleic anhydride in the presence of peroxide catalyst in a suitable organic solvent medium. The resulting base EMA copolymer can be reacted with a cross-linking agent such as loweralkyliminobis(loweralkylamine) which has two primary amine groups and leads to a cross-linked EMA copolymer. The EMA preferably is reacted with from about 3 mole % to about 7 mole % of the cross-linking agent. The desired pendant diloweralkylaminoloweralkylimide functional groups can then be incorporated into the cross-linked copolymer by reaction of diloweralkylaminoloweralkylamine with part or all of the remaining free anhydride groups of the EMA copolymer. From about 3 mole % to about 100 mole % of the diloweralkylaminoloweralkylamine is used for preparing the polyelectrolyte copolymers employed in the present invention.

A preferred diloweralkylaminoloweralkylamine is dimethylaminopropylamine and a preferred cross-linking agent is methyliminobis(propylamine).

The polyelectrolyte copolymers also can be prepared by methods which employ the aggregation step disclosed in U.S. Pat. No. 4,118,554 and any remaining free carboxyl or anhydride sites can be blocked with alkoxyalkylamine as disclosed in U.S. Pat. No. 4,157,431. Said alkoxy and alkyl preferably have from one to four carbon atoms and a most preferred blocking agent is methoxypropylamine.

It will be appreciated that disclosure of the foregoing methods of production of the polyelectrolyte copolymers is for illustrative purposes only and that the method of isolating monoclonal antibodies from cell culture media in accordance with the present invention is not limited to any particular method of their preparation.

Although the polyelectrolyte copolymers have been known to be useful for the fractionation of blood plasma and serum, and for the separation of plasma proteins from cell culture systems as seen from U.S. Pat. No. 4,382,028, they have not heretofore been known to have, or suggested to have, ability to separate monoclonal antibodies from expended cell culture media. Monoclonal antibodies are unique, highly specific materials as distinguished from polyclonal antibodies such as exist in an immunoglobulin fraction (gamma globulins). It was unexpected that such well defined, individual components could be isolated with the polyelectrolyte copolymers employed in the present invention. In prior art blood fractionation with these polyelectrolype copolymer resins as disclosed in U.S. Pat. No. 4,097,473, the gamma globulin fraction was not adsorbed by the resins but remained in solution.

The method of the present invention is adaptable to isolate monoclonal antibodies of a wide variety of types such as may be produced by culture of the corresponding hybridomas in cell culture media. Illustrative of the hybridoma antibodies which can be isolated by this method are those made against well-known, clinically important antigens such as the hormones, proteins, cell-surface antigens, tumor markers, viruses, bacteria and parasites. The hormones are illustrated by human choriogonadtropin, human somatotropin, somatostatin, somatomedin, prolactin, luteinizing hormone, follicle-stimulating hormone, thyrotropin, corticotropin, endorphins and enkephalins, melanocyte-stimulating hormone, estrogens, progestins and androgens. Proteins are illustrated by immunoglobulins G, M, A and E, interferon, fibronectin, antihemophilic factor VIII, prothrombin, plasminogen activator and alkaline phosphatase. The cell-surface antigens are illustrated by immune-associated antigens and histocompatibility antigens. Tumor markers are illustrated by carcinoembryonic antigen, α-fetoprotein and prostatic acid phosphatase. Viruses are illustrated by hepatitis, herpes and rabies viruses. Other typical clinically important antigens will be apparent to the person skilled in the art by reference to any one of the numerous review articles on monoclonal antibodies, for example, the paper by Sevier et al., *Clin. Chem.* 27 (11), 1797–1806 (1981) and references cited therein.

The present invention also is useful for the isolation of monoclonal antibodies generated against other mammalian species, e.g., bovine, porcine, equine and ovine, as well as the lower organisms.

In order to further exemplify the invention with specific illustrative hybridomas and monoclonal antibodies derived therefrom, large scale culture of three different types of hybridomas and isolation of monoclonal antibodies produced thereby is described in detail in Examples 1–3 hereinafter. These examples illustrate monoclonal antibodies against a bovine somatotropin antigen, a human melanoma associated antigen and a murine H-2 cell-surface antigen of the major histocompatibility complex (MHC).

In these examples, the bovine somatotropin hybridoma is designated F11-A1-B6-B3; the human melanoma hybridoma is designated 9.2.27; and the murine anti-H-2 hybridoma is designated 16-1-2N.

The F11-A1-B6-B3 monoclonal hybridoma was prepared by immunizing BALB/c female mice with bovine somatotropin purified from pituitary extracts (90% pure) and hybridizing the mouse spleen cells with mouse myeloma cells Sp2/0-Ag14. This is a well-known, widely-available cell line of BALB/c origin defined by Schulman et al., *Nature* 276, 269–70 (1978), the disclosure of which is incorporated herein by reference. These cells, which do not synthesize Ig chains, are available from the Basel Institute for Immunology, Basel, Switzerland, and from the American Type Culture Collection, Rockville, Md. under accession number ATCC CRL-1581.

The immunization was carried out by I.P. injection of 100–200 µg of the bovine somatotropin in Freund's complete adjuvant, with some of the mice receiving booster shots to ensure serum antibody titers as determined by standard ELISA assay (enzyme-linked immunoabsorbent assay). See Engvall and Perlmann, *Immunochemistry* 8, 871–74 (1971).

The hybridization was carried out by exposing spleen cells, after dissociation by mild mechanical disruption, and mixing with the myeloma cells in a ratio of 10:1, to 50% PEG 1500 in Dulbecco's modified Eagle's medium, low glucose, plus 50 mM HEPES buffer (N-2-hydroxyethylpiperazine-N'-2-ethanesulfonic acid), pH 7.4, for five minutes at room temperature (20°–22° C.). The PEG was removed and the cells resuspended in Dulbecco's modified Eagle's medium, high glucose, supplemented with 10% horse serum, 5% calf serum, 1X nonessential amino acids, 1X L-glutamine, 100 units/ml penicillin and 100 μg/ml streptomycin, and dispersed into tissue culture plates. Following overnight incubation at 37° C. in a humidified 7% $CO_2$ atmosphere, the medium was replaced with HAT selection medium containing 1.24 mM hypoxanthine, 0.04 mM aminopterin, and 2.06 mM thymidine. After a two week selection in the HAT medium, positive hybridoma cells were assayed by ELISA for antibodies to the bovine somatotropin and cloned in soft agar over a feeder layer of BALB 3T3 mouse cells.

The bovine somatotropin hormone antigen for producing the monoclonal antibodies also can be bovine growth hormone such as produced by genetically engineered recombinant DNA in *E. coli* as described, for example, in Eur. Pat. Appl. EP No. 75,444, Mar. 30, 1983, and in UK Pat. Appl. GB No. 2,073,245, Oct. 14, 1981. Strains of *E. coli* producing such bovine growth hormones are available from the American Type Culture Collection, Rockville, Md., under accession numbers ATCC 31826, 31840, 31841, 31842 and 31843.

The production and characterization of the monoclonal antibodies 9.2.27 are described by Reisfeld et al., *Hybridoma in Cancer Diagnosis and Treatment*, ed. by Mitchell and Oettgen, Raven Press, New York 1982, pp. 183–186; and by Bumol and Reisfeld, *Proc. Nat. Acad. Sci. USA* 79, 1245–49 (1982). The disclosure of said publications is incorporated herein by reference. These monoclonal antibodies are available from R. A. Reisfeld of the Department of Molecular Immunology, Scripps Clinic and Research Foundation, La Jolla, Calif., and from the National Cancer Institute (NCI) Frederick Cancer Research Center, Frederick, Md.

In their reported production of the 9.2.27 monoclonal antibodies, the nonsecreting (non Ig-secreting) variant 653 of P3-X63-Ag8 mouse myeloma cells was used for fusion with sensitized (immunized) BALB/c splenocytes with 30% PEG 1000 as described previously by Gefter et al., *Somatic Cell Genetics* 3, 231–34 (1977), and by Morgan et al., *Hybridoma* 1, 27–38 (1981). The P3-X63-Ag8 cell line is a well-known, mouse myeloma cell line commonly used for production of hybridomas as described by Köhler and Milstein, *Nature* 256, 495–97 (1975).

The immunogen used in producing these monoclonal antibodies was the 4 Molar urea extract obtained from M14 or M21 human melanoma cell lines. This extract from monolayer M14 human melanoma cells is described by Galloway et al., *J. Immunol.* 126, 62–66 (1981). The M21 human melanoma cell line was derived from a metastatic melanoma lesion as described by Guilano et al., *Proc. Am. Assoc. Cancer Res.* 19, 133 (1978). It has been maintained in long-term cell culture in RPMI-1640 medium supplemented with 10% fetal calf serum (GIBCO), 2 mM L-glutamine, and 50 μg/ml of gentamycin sulfate at 37° C. in a humidified 5% $CO_2$/95% air atmosphere.

The production and characterization of the monoclonal antibodies 16.1.2N are described by Ozato et al., *J. Immunol.* 124 (2), 523–540 (1980). The disclosure of said publication is incorporated herein by reference. These monoclonal antibodies are produced by a hybridoma cell line generated by fusing mouse immune lymphocytes with mouse myeloma cells. The hybridoma cell line is available from the Hybridoma Cell Bank, supported by the National Institute of Allergy and Infectious Diseases, and maintained by the American Type Culture Collection, Rockville, Md., under accession number ATCC HB 14. This cell line was produced by fusing NS-1 myeloma cells with spleen cells from C3H.SW mice previously immunized with C3H cells. The NS-1 is a nonsecreting K-chain synthesizing cell line further described by Köhler, Howe and Milstein, *Eur. J. Immunol.* 6, 292 (1976). The monoclonal antibodies produced by the 16.1.2N hybridoma are specific for $K^k$ and $D^k$ antigens but cross react with $K^{q,p,r}$.

The cell fusions to produce the 16.1.2N hybridoma were reported to be carried out essentially by the published methods of Köhler and Milstein, *Nature* 256, 495–97 (1975) and of Gefter et al., *Somatic Cell Genetics* 3, 231–34 (1977). Hybrid selection was made in HAT medium essentially according to Littlefield, *Exp. Cell Res.* 41, 190 (1966).

Other illustrative monoclonal antibodies which can be grown in cell culture and isolated by the method of the present invention are, for example:

(1) Monoclonal antibodies against Herpes simplex types 1 and 2 (HSV types 1 and 2) produced from hybridoma cells 3El and 1D4 available under ATCC Nos. HB 8067 and HB 8068, respectively, as described in U.S. Pat. No. 4,430,437, and monoclonal IgM antibodies against HSV as disclosed in Eur. Pat. Appl. EP No. 100,955, Feb. 22, 1984.

(2) Monoclonal antibodies agianst porcine Factor VIII coagulant protein as described by Fass et al., *Blood* 59(3), 594–600 (1982), and against human Factor VIII:C as disclosed by Muller et al., *Blood* 58(5), 1000–06 (1981).

(3) Monoclonal antibodies against human factor VIII/von Willebrand protein complex using hybridomas prepared from mouse myeloma cell lines P3-X63-Ag8 and Sp2/0-Ag14, as described by Sola et al., *Proc. Natl. Acad. Sci. USA* 79, pp. 183–87 (1982).

(4) Monoclonal antibodies against alpha interferon (leukocyte interferon) as described in U.S. Pat. No. 4,423,147.

(5) Monoclonal antibodies against prothrombin produced from hybridomas of immunized mouse spleen cells fused with NS-1 mouse myeloma cells as described by Lee et al., *Protides Biol. Fluids* 30, 395–8 (1982).

(6) Monoclonal antibodies against human T-lymphocytes as described in U.S. Pat. No. 4,381,292.

(7) Monoclonal antibodies against plasminogen activator as described by Nielsen et al., *EMBO J.* 2(1) 115–19 (1983).

(8) Monoclonal antibodies against human suppressor T cells produced by hybridoma ATCC CRL-8014 as described in U.S. Pat. No. 4,361,550.

(9) Monoclonal antibodies against human peripheral T cells produced by hybridoma ATCC CRL-8000 as described in U.S. Pat. No. 4,363,799.

(10) Monoclonal antibodies against carcinoembryonic antigen (CEA) produced by hybridoma ATCC CRL-8019 as described in U.S. Pat. No. 4,349,528.

(11) Monoclonal antibodies against hepatitis B virus as described in Eur. Pat. Appl. EP No. 38,642, Oct. 28, 1981, and against hepatitis B surface antigen as described in PCT Int. Appl. WO No. 82 01,072, April 1, 1982.

(12) Monoclonal antibodies against human growth hormone as described by Ivanyi and Davies, *Mol. Immunol.* 1 17, 287–90 (1980).

(13) Monoclonal antibodies against surface antigens of T cells as described in U.S. Pat. No. 4,443,427.

(14) Monoclonal antibodies against bacterial antigens produced by hybridoma ATCC HB8178 as disclosed in U.S. Pat. No. 4,443,549.

(15) Monoclonal antibodies against human follicle-stimulating hormone as disclosed in Fr. Demande FR No. 2,489,152, Mar. 5, 1982.

(16) Monoclonal antibodies against human luteinizing hormone as disclosed in FR Demande FR No. 2,489,151, Mar. 5, 1982.

(17) Monoclonal antibodies against human colon carcinoma as disclosed by Kaszubowski et al., *Cancer Res.* 44(3), 1194–9 (1984), and designated as CCOL1.

(18) Monoclonal antibodies against human factor IX as described by Smith et al., *Thromb. Res.* 33(2), 211–24 (1984).

General methods and large scale equipment for growing the hybridoma cells to produce the above and other such monoclonal antibodies are described by the reports of Feder and Tolbert, *Sci. Amer.* 248 (1), 24–31 (1983); and Tolbert and Feder, *Annual Reports on Fermentation Technology*, Ch. 3, pp. 35–74, Academic Press Inc., 1983. The disclosures of said reports are incorporated herein by reference.

Conventional cell culture media such as, for example, RPMI-1640, Dulbecco's modified Eagle's medium, and the like as described by Morton, *In Vitro* 6(2), 89–108 (1970), can be used for culture of the hybridoma cells.

The hybridoma cells can be maintained over long periods of time in a substantially arrested state of proliferation with continuous secretion of monoclonal antibodies in the static maintenance reactor (SMR) system of co-pending application Ser. No. 447,748, filed Dec. 8, 1982, and assigned to the Common Assignee. The disclosure of said patent application is incorporated herein by reference.

Following growth and/or maintenance of the hybridoma in cell culture medium, the contacting of the spent cell culture medium, or a concentrate thereof, containing the monoclonal antibodies with the polyelectrolyte resin for adsorption is carried out at a pH of from about 6.5 to about 7.5 at an ionic salt concentration of from about 0.01 to about 0.15 molar (preferably from about 0.01 to about 0.04 molar). Alkali metal, alkaline earth metal and ammonium salts are preferred, especially sodium and potassium. Use of sodium chloride is most preferred.

Protein adsorbed on the polyelectrolyte resin can be retained in bound form or can be subjected to desorption (elution) by adjusting to a pH of from about 4.7 to about 5.5 (preferably about 5) at an ionic salt concentration of from about 0.01 to about 0.15 molar (preferably from about 0.01 to about 0.04 molar) to produce an antibody-rich fraction in the eluant (filtrate). Retention of the monoclonal antibody in a form bound to the polyelectrolyte copolymer may be useful for diagnostic purposes.

When the antibody-rich fraction shows β-globulin contamination upon assay, said fraction can be subjected to salt fractionation at a pH of from about 6.5 to about 7.5 (preferably about 7) to form a precipitate of essentially pure monoclonal antibody. Alkali metal, alkaline earth metal and ammonium salts are preferred, especially ammonium sulfate. Use of from about 2 molar to about 2.4 molar ammonium sulfate for the salt fractionation is most preferred.

Separation of solid from liquid phases in the above adsorption and desorption steps can be carried out by conventional filtration and/or centrifugation followed by washing of the separated solid material. Salt concentrations can be reduced by dialysis, ultrafiltration, and/or dilution. Adjustments in pH can be made by treatment with conventional acids and bases such as, for example, citric acid, sodium hydroxide and ammonium hydroxide or by use of well-known buffer materials such as phosphate buffered saline (PBS).

The polyelectrolyte copolymers used in Examples 1 to 3 were copolymers of ethylene and maleic anhydride in a molar ratio of about 1:1 of the component monomers, polymerized to a molecular weight of about 100,000, cross-linked with about 5 mole percent (based on the reactive sites on the copolymer) of methyliminobispropylamine and derivatized with dimethylaminopropylamine (90 mole % with polyelectrolyte A and 80 mole % with polyelectrolyte B). In the case of polyelectrolyte B, the remaining reactive sites were blocked with methoxypropylamine. The derivatized copolymers were converted to the hydrochloride salt form, filtered and dried. Results with polyelectrolyte A are shown in Tables 1 to 8 and with polyelectrolyte B in Table 9, below. Other salt forms as well as the base form of the polyelectrolyte copolymers can be used in the method of the invention.

Prior to use, the dried polyelectrolyte copolymers (20 grams) were slurried in 0.02 M HCl in 0.01 M NaCl overnight. The resins were then filtered, slurried in one liter 0.01 M NaCl and the pH adjusted to 7.0 with 1 N NaOH. The resins were then filtered and washed with one liter of 0.01 M NaCl. As thus prepared, the resins were used for the adsorption step in Examples 1 to 3, below.

Although specific materials and conditions are described, above, and in the following examples, it will be appreciated that the invention is not limited to these specific materials, conditions and examples which are presented for illustrative purposes and not for limitation.

EXAMPLE 1

9.2.27 Hybridoma Culture 9.2.27 hybridoma cells were carried in culture at 37° C. in Dulbecco's modified Eagle's medium (DMEM) supplemented with 6% fetal bovine serum (FBS) with 4 mM L-glutamine. The cells were split approximately 1:4 in 6% FBS-DMEM upon reaching a density of 2 ml/liter PCV (packed cell volume) and in a volume sufficient to inoculate both 12 and 40 liter continuous culture perfusion reactors of the type described in U.S. Pat. No. 4,289,854. PCV was measured by the published assay method of Tolbert, Hitt and Feder, *Anal. Biochem.* 106, 109–13 (1980).

Several runs of the 9.2.27 hybridoma cell culture were also maintained in a static maintenance reactor system as described in co-pending application Ser. No. 447,748, filed Dec. 8, 1982. Perfusion reactors of the type described in U.S. Pat. No. 4,289,854 were perfused at a rate of 5 ml medium per ml packed cell volume/hr. The culture pH was metered and maintained by overlay of from about 2% to about 8% $CO_2$ in air or a sterile mixture of one part 0.5 M NaOH plus one part 0.5 M $NaHCO_3$. The hybridoma required that the medium be sparged with oxygen at a rate to maintain a fine layer of $O_2$ bubbles on top of the medium (about 1–3 ml/min).

The filtered effluent conditioned medium (spent medium) was concentrated by use of a commercially available hollow fiber concentrator (Amicon), with the 10,000 or 30,000 molecular weight cutoff in various batches. The effluent medium in each batch was concentrated approximately fifty-fold. The NaCl concentration was reduced below 0.04 M by diluting the concentrate with sterile water and repeating the concentration. The conditioned medium concentrate was stored frozen until needed for the next step.

Adsorption

Conditioned medium concentrate containing 6 gms protein was added to 20 gms filtered polyelectrolyte copolymer resin A (as defined above) and the volume made up to one liter with 0.01 M NaCl. The salt concentration of the medium was maintained below about 0.04 M to insure maximum adsorption of serum proteins to resin. The pH was maintained at 7. The resin was filtered after mixing 15 minutes at pH 7.0.

Desorption

Seven hundred fifty ml 0.01 M NaCl were added to the above filtered resin. The pH of the slurry was adjusted to pH 5.1 to 5.25 with 1 N citric acid. The resin was filtered to provide a monoclonal antibody-rich filtrate fraction in which β-globulin was found by assay to be the major contaminant. This filtrate was designated the pH 5 fraction.

Salt Fractionation

The above filtered fraction (pH 5 fraction) was brought to 2.0 M in ammonium sulfate (taking care to add the additional ammonium sulfate needed to compensate for the increase in volume). Ammonium hydroxide (1N) was added at a rate of 0.15 ml for each gram of ammonium sulfate added to maintain the mixture at about pH 7. The mixture was stirred for 30 min at 4° C. and centrifuged at 13,000×g for 30 min. The resulting monoclonal antibody containing precipitate was dissolved in PBS at one-tenth the volume of the original filtered fraction (from the desorption step) prior to ammonium sulfate addition. The antibody was concentrated twice to one-tenth the volume and resuspended in PBS to eliminate the ammonium sulfate with a Pellicon ® membrane concentrator (10,000 molecular weight membrane cutoff). The antibody was sterile filtered through a 0.2μ filter and stored at 4° C.

EXAMPLE 2

F11-A1-B6-B3 Hybridoma Culture

F11-A1-B6-B3 hybridoma cells were cultured and monoclonal antibody recovered under the same conditions as described in Example 1, above, except that (a) the cells were cultured in RPMI-1640:DMEM (1:1) supplemented with 6% or 2% FBS; (b) cells were cultured only in the 12 liter perfusion system; and (c) conditioned medium (spent medium) was concentrated on a Pellicon membrane concentrator (Millipore Corporation) with a 10,000 molecular weight cutoff.

EXAMPLE 3

16-1-2N Hybridoma Culture 16-1-2N hybridoma cells were cultured and monoclonal antibodies recovered under the same conditions as described in Example 1, above, in the 12 liter perfusion system except that the conditioned medium (spent medium) was concentrated on a Pellicon membrane concentrator with a 10,000 molecular weight cutoff.

Samples of initial culture media (at beginning of culture period), conditioned media concentrates (at end of culture period) and isolated monoclonal antibodies from the conditioned medium concentrates (after treatment with polyelectrolyte resins) in the above Examples 1 to 3 were assayed by conventional methods of agarose gel electrophoresis, Lowry protein assay and ELISA antibody assay procedures as follows.

Electrophoresis

Agarose gel electrophoresis in barbital buffer at pH 8.0, followed by Coomassie Brilliant Blue R staining, was used for identification of presence of serum proteins and antibody present in the samples before and after antibody isolation by treatment with the polyelectrolyte copolymer resins. The electrophoresis procedure was carried out on Corning electrophoresis equipment ACl (Fisher Scientific Co.). Samples taken directly from the cell culture were concentrated 25 to 50-fold using a Minicon ® B 15 concentrator having a 15,000 molecular weight cut-off (Amicon Corporation) prior to application to the gel for electrophoresis.

One μl samples were injected into wells of an agarose Universal plate (1% agarose, 5% sucrose, 0.035% EDTA in 0.065 M barbital buffer, pH 8.6). The plate was electrophoresed for 30 min at 90 volts potential against 0.05 M barbital buffer containing 0.035% EDTA at pH 8.6. The plates were fixed for 10 min in sulfosalicylic acid (200 g/liter of $H_2O$) and stained with Coomassie Brilliant Blue R (Sigma Chemical Co.) (2.5 g/liter of 5% acetic acid) for 2 hrs. Plates were washed in changes of water. After air drying, the plates were read on a Gelman ACD 15 densitometer at 600 mM.

Protein Assay

Protein concentrations were determined by the method of Lowry et al., *J. Biol. Chem.* 193, 265–75 (1951). Protein samples containing 5 to 50 μg protein along with 5, 10, 25, 50 and 100 μl of 0.05 mg/ml bovine serum albumin standard were added to 100 μl of 1N NaOH. One ml of 0.02% $CuSO_4$ and 0.04% sodium tartrate in 2% $Na_2CO_3$ was added to each sample. Fifty μl of 2 N Folin phenol reagent (Fisher Scientific) were added to each tube. After 30 min at room temperature, samples were read at 750 mμ on a Gilford 260 spectrophotometer. Blanks contained all reagent except sample and standards.

ELISA Antibody Assay

Enzyme-linked immunosorbent assay (ELISA) using alkaline phosphatase as the conjugated enzyme was carried out by the method of Engvall et al., *Immunochemistry* 8, 871–4 (1971). Analyses of the 9.2.27 and 16-1-2N antibodies were carried out in multi-welled plates coated with goat anti-mouse F(ab')2 (Cappel Laboratories). The wells were inoculated with dilution of said antibodies or with a protein A-purified 9.2.27 monoclonal antibody standard. Wells were washed and inoculated with alkaline phosphatase conjugated with goat-anti-mouse Ig ($\gamma$, $\mu$, $\alpha$, $\kappa$, $\lambda$) IgG. The bound enzyme was assayed using paranitrophenyl phosphate and reading the p-NO$_2$-phenol produced in the well with a Microelisa® Mini Reader MR590 at 410 m$\mu$ (Dynatech Laboratories, Inc.)

Analysis of the bovine somatotropin antibody F11-A1-B6-B3 was carried out by adsorbing the hormone to the multi-welled plates. F11-A1-B6-B3 purified by protein A from ascites fluid was used as standard. The same alkaline phosphatase conjugated goat-anti-mouse antibody and paranitrophenyl phosphate substrate were used to detect the monoclonal antibody bound.

Table 1, below, shows the relative percentage of protein in (a) the starting culture medium, supplemented with 6% fetal bovine serum, and (b) the conditioned media (spent media) concentrated fifty-fold from 9.2.27, F11-A1-B6-B3 and 16-1-2N hybridoma growth as determined by electrophoresis.

Tables 2–4, below, present tabulations of concentrates of conditioned media used in the antibody isolations, giving their protein concentration, percentage of major proteins and the serum percentage used in culturing the hybridoma. The 9.2.27 hybridoma shown in Table 2 was cultured in both the continuous culture system (CCS) and in the static maintenance reactor (SMR) while the F11-A1-B6-B3 and 16-1-2N hybridomas shown in Tables 3 and 4 were cultured only in the continuous culture system (CCS). Antibody production was maintained at serum concentration levels lower than the conventional 6% serum level. In the case of the 9.2.27 hybridoma the serum concentration was as low as 0.25% FBS. Production of antibody was also observed on the SMR using 5% Synmed in DMEM. Synmed is a commercially produced serum-free medium supplemented with bovine albumin, porcine insulin and human transferin, available from Centaurus Corp., Anaheim, Calif.

When the conditioned medium concentrates were contacted with polyelectrolyte resin A at pH 7, the majority of the protein was adsorbed on the resin. At a protein charge to resin of 0.3 grams protein per gram of resin in 0.01 M NaCl, essentially all the antibody, $\beta$, $\alpha_2$ and albumin was adsorbed to the resin. Electrophoreses of the pH 7.0 unadsorbed material concentrated fifty-fold showed no antibody or albumin.

TABLE 1

RELATIVE PERCENTAGE OF PROTEINS IN CULTURE MEDIUM AND CONDITIONED MEDIUM FROM HYBRIDOMA CULTURE OF F11-A1-B6-B3, 9.2.27 AND 16-1-2N

| Medium | Antibody | $\beta$ Globulin | $\alpha_2$-Globulin | Albumin |
|---|---|---|---|---|
| Starting | | 23.0 | 46.5 | 30.1 |
| 9.2.27* | 10.6 | 15.3 | 39.5 | 34.2 |
| F11-A1-B6-B3* | 8.7 | 23.7 | 16.3 | 49.5 |
| 16-1-2N++ | 17.4 | 18.5 | 19.8 | 43.4 |

*Original culture medium was supplemented with 2% fetal bovine serum and concentrated fifty-fold after it was used to culture the hybridomas (spent medium).
++Original culture medium was supplemented with 6% fetal bovine serum and concentrated fifty-fold after it was used to culture the hybridoma (spent medium).

TABLE 2

9.2.27 CONCENTRATES USED FOR ISOLATION OF ANTIBODY

| Concentrate Run | Percentage Serum In Culture | Protein Concentration (g/L) | Percentage Protein Components* | | | | Growth System |
|---|---|---|---|---|---|---|---|
| | | | Antibody | $\beta$ | $\alpha_2$ | Albumin | |
| 674 | 2 | 46.8 | 14.0 | 21.0 | 36.2 | 28.5 | CCS |
| 675 | 2 | 28.1 | 10.4 | 20.0 | 38.8 | 30.9 | CCS |
| 679 | 0.5 | 18.5 | 11.2 | 19.6 | 37.3 | 30.9 | CCS |
| 682 | 0.5 | 11.5 | 11.5 | 17.6 | 35.9 | 34.3 | SMR |
| 684 | 0.5 | 6.4 | 7.8 | 15.6 | 39.7 | 35.5 | SMR |
| 689 | 0.25 | 11.88 | 21.6 | 17.9 | 31.6 | 28.0 | SMR |
| 691 | 0.25 | 7.38 | 12.4 | 17.2 | 35.6 | 34.7 | SMR |
| 692 | S.F. | 1.43 | 34.35 | 20.4 | | 45.2 | SMR |

*Determined by agarose electrophoresis
CCS = continuous culture system
SMR = static maintenance reactor
S.F. = serum-free media supplemented with 5% Synmed

TABLE 3

F11-A1-B6-B3 CONCENTRATES USED FOR ISOLATION OF MONOCLONAL ANTIBODY

| Concentrate Run | Percentage Serum In Culture | Protein Concentration (g/L) | ELISA Antibody mg/L | Percentage Protein Components* | | | |
|---|---|---|---|---|---|---|---|
| | | | | Antibody | $\beta$ | $\alpha_2$ | Albumin |
| 477 | 6 | 42.0 | 416 | | | | |
| 480 | 2 | 22.3 | 870 | 10.91 | 19.69 | 31.25 | 37.45 |
| 492 | 2 | 47.2 | 1440 | | | | |

*Determined by agarose electrophoresis

TABLE 4

16-1-2N CONCENTRATES USED FOR ISOLATION OF MONOCLONAL ANTIBODY

| Concentrate Run | Percentage Serum In Culture | Protein Concentration (g/L) | ELISA Antibody mg/L | Percentage Protein Components* | | | |
|---|---|---|---|---|---|---|---|
| | | | | Antibody | $\beta$ | $\alpha_2$ | Albumin |
| 838 | 6 | 105.2 | 7.2 | 17.4 | 18.5 | 19.8 | 43.4 |

*Determined by agarose electrophoresis

Extraction of the protein bound resin in 0.01 M NaCl with the pH adjusted to a range of about 5.0 to 5.2 with citric acid produced an antibody rich fraction with β globulin as the main contaminate. Careful maintenance of pH produced a fraction containing about 60% antibody when starting with the 9.2.27, F11-A1-B6-B3 and 16-1-2N conditioned medium concentrates, as shown in Tables 5, 7 and 8, below. Table 5 also shows the comparison of the antibody recovered for eight separate purifications of 9.2.27 concentrates. The concentrates used for isolation were combinations of the concentrates listed in Table 2 at the amount to give the desired final protein concentration. The grams of antibody given as the starting amount of antibody were obtained by multiplying the percentage of antibody obtained from agarose electrophoresis ACD 15 scan by the protein assay of the sample.

Table 6, below, shows the 9.2.27 antibody recovered as determined by ELISA assay. Table 7 gives the recovery of the bovine somatotropin antibody in the pH 5 fraction. The analytical data were obtained by ELISA analysis. Table 8 gives the antibody recovery of the pH 5 isolate of 16-1-2N antibody.

TABLE 5

ISOLATION OF MONOCLONAL ANTIBODY FROM 9.2.27 CONDITIONED MEDIUM CONCENTRATES

| Purification Run | PE+ Grams | Protein Grams | Antibody Starting gm* | Antibody Recovery pH 5 Fraction | | |
|---|---|---|---|---|---|---|
| | | | | Grams Protein | Purity (%) | Grams Antibody* |
| 418 | 120 | 36.6 | 5.1 | 2.46 | 55.6 | 1.37 |
| 421 | 120 | 35.1 | 4.9 | 3.17 | | |
| 426 | 120 | 37.9 | 5.3 | 3.59 | 50.9 | 1.83 |
| 429 | 240 | 73.3 | 9.0 | 3.55 | 50.7 | 1.80 |
| 433 | 230 | 36.0 | 4.1 | 3.73 | 45.3 | 1.69 |
| 436 | 120 | 35.4 | | 4.49 | 55.1 | 2.47 |
| 441 | 120 | 43.0 | | 3.77 | 47.3 | 1.79 |
| 445 | 120 | 10.4 | 2.3 | 2.73 | 73.5 | 2.01 |

*Grams antibody determined by percentage antibody by agarose electrophoresis × total Lowry protein.
+Polyelectrolyte copolymer resin A

TABLE 6

9.2.27.54 ANTIBODY RECOVERY BY ELISA

| Purification Run | Conditioned Medium Concentrate Run | Antibody g/L* | Antibody Starting gm | Antibody Recovery pH 5 Fraction gms |
|---|---|---|---|---|
| 421 | 674 | 2.57 | 1.92 | 2.53 |
| 429 | 674 | 3.78 | 2.83 pooled as 4.36 | 3.23 |
| | 675 | .87 | .70 | |
| | 679 | 1.11 | .83 | |
| 426 | 674 | 2.32 | 1.87 | 1.86 |

*Determined by ELISA

TABLE 7

F11-A1-B6-B3 ANTIBODY RECOVERY BY ELISA

| Purification Run | Conditioned Medium Concentrate | | PE+ gm | Antibody Starting mg | Antibody pH 5 Fraction mg |
|---|---|---|---|---|---|
| | Run | % Serum(*) | | | |
| 482 | 477 | (6%) | 2.0 | 5.40 | 3.36 |
| 482 | 477 | (2%) | 2.0 | 26.45 | 16.65 |
| 489 | 480 | (2%) | 20.0 | 235.00 | 217.80 |
| 498 | 402 | (2%) | 20.0 | 187.20 | 56.80 |

(*)Percent fetal bovine serum used to culture cells.
+Polyelectrolyte copolymer resin A

TABLE 8

16-1-2N ANTIBODY RECOVERY BY ELISA

| Purification Run | PE+ gm | Protein gm | Antibody Starting gm* | Antibody Recovery pH 5 Fraction | |
|---|---|---|---|---|---|
| | | | | gm* | Purity (%)** |
| 838 | 20 | 6 | .43 | .30 | 72 |

*Determined by ELISA
**Determined by electrophoresis
+Polyelectrolyte copolymer resin A Table 9, below, shows results of F11-A1-B6-B3 antibody isolation with the polyelectrolyte copolymer resin B (as defined above). The 50% recovery of antibody in the pH 5 fraction was equivalent to that observed with polyelectrolyte copolymer resin A.

TABLE 9

F11-A1-B6-B3 ANTIBODY RECOVERY BY ELISA

| Run | Conditioned Medium Concentrate (I) % Serum | PE+ gm | Antibody Starting mg* | Antibody Recovery pH 5 Fraction | |
|---|---|---|---|---|---|
| | | | | mg* | Purity (%)** |
| 492 | (2%) | 10 | 79.5 | 72.4 | 50.3 |

*Determined by ELISA
**Determined by electrophoresis
+Polyelectrolyte copolymer resin B Three purification runs from Table 5 were subjected to analysis for the presence of endotoxin, namely runs 429, 433 and 436. Standard Limulus Amebocyte Lysate tests were conducted on the starting conditioned medium concentrates, the filtrates from the adsorption with resin at pH 7 and the filtrates from the desorption at pH 5. This is an in vitro test based on the gelling of a pyrogenic preparation in the presence of the lysate of the amebocytes of the horseshoe crab (Limulus polyphemus) which detects endotoxic pyrogens of gram-negative bacteria. The results set forth in Table 10, below, showed a significant decrease in the level of endotoxin by virtue of its adsorption on the resin at pH 7 without desorption at pH 5. Removal of these endotoxins is desirable for therapeutic uses of the monoclonal antibodies.

TABLE 10

ENDOTOXIN ANALYSIS OF 9.2.27 ANTIBODY ISOLATION SAMPLES
Amount of Endotoxin (nanograms)*

| Purification Run | Conditioned Medium Concentrate | pH 7 filtrate | pH 5 filtrate |
|---|---|---|---|
| 429 | 30.00 | 0.18 | 1.20 |
| 433 | 16.75 | 0.25 | 0.92 |
| 436 | 24.38 | 0.26 | 1.04 |

*Analysis by Associates of Cape Cod, Inc. Wood Hole, Massachusetts

Various other examples will be apparent to the person skilled in the art after reading the present disclosure without departing from the spirit and scope of the invention and it is intended that all such other examples be include within the scope of the invention.

What is claimed is:

1. A method of isolating monoclonal antibodies from spent culture medium of the in vitro growth of hybridoma cells comprising treating said spent cell culture medium or a concentrate thereof by adsorption with a water-insoluble, cross-linked polyelectrolyte copolymer of olefinically unsaturated monomer having from 2 to about 4 carbon atoms and α,β-unsaturated polycarboxylic acid or anhydride having from 4 to about 6 carbon atoms containing pendant diloweralkylaminoloweralkylimide functional groups.

2. The method of claim 1 in which the olefinically unaturated monomer is ethylene and the α,β- unsaturated polycarboxylic acid or anhydride is maleic acid or anhydride.

3. The method of claim 2 in which the diloweralkylaminoloweralkylimide is dimethylaminopropylimide.

4. The method of claim 3 in which the polyelectrolyte copolymer contains from about 3 mole % to about 100 mole % of said dimethylaminopropylimide.

5. The method of claim 1 including the additional step of desorption of protein adsorbed to said polyelectrolyte copolymer.

6. The method of claim 1 in which the adsorption is carried out at a pH of from about 6.5 to about 7.5 and an ionic salt concentration of from about 0.01 to about 0.15 molar.

7. The method of claim 5 in which the desorption is carried out at a pH of from about 4.7 to about 5.5 and an ionic salt concentration of from about 0.01 to about 0.15 molar.

8. The method of claim 6 in which the desorption is carried out at a pH of from about 4.7 to about 5.5 and an ionic salt concentration of from about 0.01 to about 0.15 molar.

9. A method of isolating monoclonal antibodies from spent culture medium of the in vitro growth of hybridoma cells comprising treating said spent cell culture medium or a concentrate thereof by adsorption with a water-insoluble, cross-linked polyelectrolyte copolymer of ethylene and maleic acid or anhydride and containing from about 3 mole % to about 100 mole % of pendant dimethylaminopropylimide functional groups followed by desorption of protein adsorbed to said polyelectrolyte copolymer, said adsorption being carried out at a pH of from about 6.5 to about 7.5 and an ionic salt concentration of from about 0.01 to about 0.04 molar and said desorption being carried out at a pH of from about 4.7 to about 5.5 and a ionic salt concentration of from about 0.01 to about 0.04 molar.

10. The method of claim 5 including the additional step of subjecting the desorbed protein to salt precipitation.

11. The method of claim 8 including the additional step of subjecting the desorbed protein to salt precipitation.

12. The method of claim 10 in which the precipitant salt is ammonium sulfate.

13. The method of claim 11 in which the precipitant salt is ammonium sulfate.

14. A method of isolating monoclonal antibodies from spent culture medium of the in vitro growth of hybridoma cells comprising treating said spent cell culture medium or a concentrate thereof by adsorption with a water-insoluble, cross-linked polyelectrolyte copolymer of ethylene and maleic acid or anhydride and containing from about 3 mole % to about 100 mole % of pendant dimethylaminopropylimide functional groups followed by desorption of protein adsorbed to said polyelectrolyte copolymer and thereafter subjecting said desorbed protein to salt precipitation, said adsorption being carried out at a pH of from about 6.5 to about 7.5 and an ionic salt concentration of from about 0.01 to about 0.04 molar, said desorption being carried out at a pH of from about 4.7 to about 5.5 and an ionic salt concentration of from about 0.01 to about 0.04 molar and in which the precipitant salt is from about 2 to about 2.4 molar ammonium sulfate.

15. Monoclonal antibody bound to polyelectrolyte copolymer as defined in claim 1.

* * * * *